United States Patent
Dumitrescu et al.

(10) Patent No.: US 7,687,034 B2
(45) Date of Patent: Mar. 30, 2010

(54) VALVE SEALING SYSTEM FOR A REAGENT PACKAGE

(75) Inventors: Nicolae Dumitrescu, Stamford, CT (US); Joseph Carlucci, Harrison, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1154 days.

(21) Appl. No.: 11/087,240

(22) Filed: Mar. 23, 2005

(65) Prior Publication Data

US 2006/0216210 A1     Sep. 28, 2006

(51) Int. Cl.
*B01L 3/00* (2006.01)
*B01F 15/02* (2006.01)
*G01N 35/10* (2006.01)

(52) U.S. Cl. .................. 422/102; 422/103; 220/203.11; 251/298; 251/303; 251/333; 251/334; 251/364

(58) Field of Classification Search .................. 422/99, 422/102, 103; 251/298, 303, 333, 334, 900, 251/364; 215/45, 87; 220/203.01, 203.09, 220/203.11, 203.12
See application file for complete search history.

(56) References Cited

U.S. PATENT DOCUMENTS

| | | | | |
|---|---|---|---|---|
| 5,101,853 A | * | 4/1992 | Mailliet et al. | 137/242 |
| 6,043,097 A | * | 3/2000 | Dumitrescu et al. | 436/48 |
| 6,197,260 B1 | * | 3/2001 | Bradshaw et al. | 422/101 |
| 6,440,371 B1 | * | 8/2002 | Dumitrescu et al. | 422/101 |
| 6,511,634 B1 | * | 1/2003 | Bradshaw et al. | 422/102 |

* cited by examiner

*Primary Examiner*—Jill Warden
*Assistant Examiner*—Cedric Chan

(57) ABSTRACT

The valve sealing system for a reagent package includes an annular cylindrical gasket seated in a channel formed in the package. A rocker valve on the package pivots relative to the annular cylindrical gasket which surrounds an opening to the chamber of the reagent package. The annular channel includes a radially inner peripheral channel sidewall, a radially outer peripheral channel sidewall, and a bottom portion. An inclined peripheral wall portion of the channel intersects one of the channel sidewalls at an obtuse angle and the bottom portion of the channel. When the rocker valve is in a valve closed position it engages the annular cylindrical gasket to provide a substantially leak-tight seal.

21 Claims, 5 Drawing Sheets

VALVE SEALING SYSTEM FOR A REAGENT PACKAGE

BACKGROUND OF THE INVENTION

This invention is directed to reagent packages having valve controlled openings and more particularly to a novel valve sealing system for a reagent package.

Reagent packages such as shown in U.S. Pat. Nos. 6,043,097 and 6,511,634 include at least one chamber that can hold two ingredients intended for later mixing within the reagent package, separate from each other, until the mixing of such ingredients is desired. For example, as disclosed in U.S. Pat. No. 6,043,097, a reagent package holds a reagent in powder form and also contains, in a sealed glass ampoule, a selected amount of reconstituting liquid ingredient for the powder reagent.

It should be noted that the reagent packages shown in U.S. Pat. Nos. 6,043,097 and 6,511,634 are dual packages formed as an integral unit. Each package is similar in structure and function and has a separate packaging section arranged side by side. The packaging sections are non-communicable.

Since each packaging section is similar in structure and function, only one of the packaging sections will be described herein and the term reagent package will be used synonymously with the term packaging section unless otherwise indicated.

When it is desired to reconstitute the powder reagent into a liquid reagent the glass ampoule with the reconstituting liquid is crushed within the reagent package. The reconstituting liquid, although liberated from the broken ampoule, remains confined within the reagent package where it can intermix within the reagent package with the dry powder reagent. The dry powder reagent is thus reconstituted in liquid form within the reagent package. The reagent package can then serve as a reservoir to supply the reconstituted liquid reagent to a known sample analysis system.

The reagent package previously referred to includes an opening in a lid of the package through which a liquid reagent is aspirated from the chamber of the reagent package. The opening in the lid is also referred to as the chamber opening or package opening. The reagent package also includes a filter in the chamber that prevents broken glass from being aspirated with the liquid reagent.

In the previously cited patents the opening of the reagent package is closable by a rocker valve. The rocker valve is pivotable from a valve closed position, that provides a substantially leak tight seal of the package opening, to a valve open position wherein the package opening is accessible by an aspiration device. Aspiration of reagent from the reagent package is usually made in amounts needed to provide desired reactions with other agents in a known sample analysis system. For example, an aspiration of 4 microliters of reagent is feasible for sustaining a reaction that will yield or lead to definitive data in analyzing the blood chemistry of an individual.

The chamber of a known reagent package of the type previously referred to can be provided with approximately 20 to 22 ml of reagent. This amount of reagent is sufficient to supply a predetermined aspiration quantity that permits at least 1,250 separate aspirations of reagent.

Because the reagent in a reagent package is known to be extremely costly, it is desirable to minimize evaporation of reagent whenever possible, especially from the opening of the reagent chamber. It is also desirable to avoid the risk of reagent contamination that might occur if the opening to the reagent chamber were left in a continuously open condition. Therefore, the rocker valve of the reagent package is usually kept in a valve closed position before and after each aspiration of the reagent. The rocker valve is thus maintained in a valve open condition only for the duration of time needed to aspirate reagent. After a reagent aspiration cycle is completed the rocker valve is kept in a valve closed position until another reagent aspiration cycle is begun.

Thus the number of times the rocker valve on the reagent package is pivoted from a valve closed position to a valve open position corresponds to the number of aspiration cycles, such as for example, approximately 1,500 times, corresponding to approximately 1,500 cycles of reagent aspiration from the reagent package.

A known valve sealing arrangement between the rocker valve and the opening to the reagent chamber, when the rocker valve is in a valve closed position, includes an "O" ring valve seal that surrounds the chamber opening. Preferably the "O" ring is in a fixed position and the rocker valve pivots relative to the surface of the "O" ring. The rocker valve includes a valve face that confronts the opening to the chamber of the reagent package and remains in contact with the "O" ring when the rocker valve is in the valve closed position to provide a seal around the opening to the reagent chamber.

Known "O" rings in previous use are circular in cross section, where the sectional cutting plane is perpendicular to the plane of the "O" ring. A valve seal is produced when the "O" ring is compressed a predetermined amount by the valve face of the rocker valve. Generally the greater the compression of the "O" ring by the valve face, the more effective the seal becomes between the valve face and the "O" ring.

The "O" ring thus cooperates with the valve face of the rocker valve to provide a substantially leak tight seal between the rocker valve and the reagent chamber when the rocker valve is in the valve closed position.

Opening and closing of the rocker valve is preferably automated using an air cylinder with an actuating arm that engages the rocker valve with a predetermined force to pivot the valve from a valve closed position to a valve open position and vice versa. The force supplied by the actuating arm to the rocker valve must overcome the frictional force due to compression of the "O" ring by the valve face when the rocker valve is moved between the valve closed position and the valve open position.

It has been found desirable in a sample analysis system to limit the valve actuation force that is needed to open and close the rocker valve to an amount that is below 2 lbs. maximum. It is also desirable that the seal between the rocker valve and the "O" ring in a valve closed position should limit evaporation of reagent from the reagent package to a rate that is less than 0.05% per day. These system requirements have been difficult to attain with previously used "O" rings.

One problem is that in order to maintain a system evaporation rate of less than 0.05% of reagent per day the valve face compression of the "O" rings requires an actuation force in excess of 2 lbs to pivot the rocker valve from the valve closed position to the valve open position and vice-versa.

It is thus desirable to provide a valve sealing system for a reagent package that permits usage of a reagent valve actuation force of approximately 1.5 lbs. yet provides a seal between the rocker valve and the reagent package chamber that maintains a reagent evaporation rate of less than 0.05% per day.

DESCRIPTION OF THE DRAWINGS

In the accompanying drawings.

Corresponding reference numbers indicate corresponding parts throughout the several views of the drawings.

DETAILED DESCRIPTION OF THE INVENTION

Figure 1:
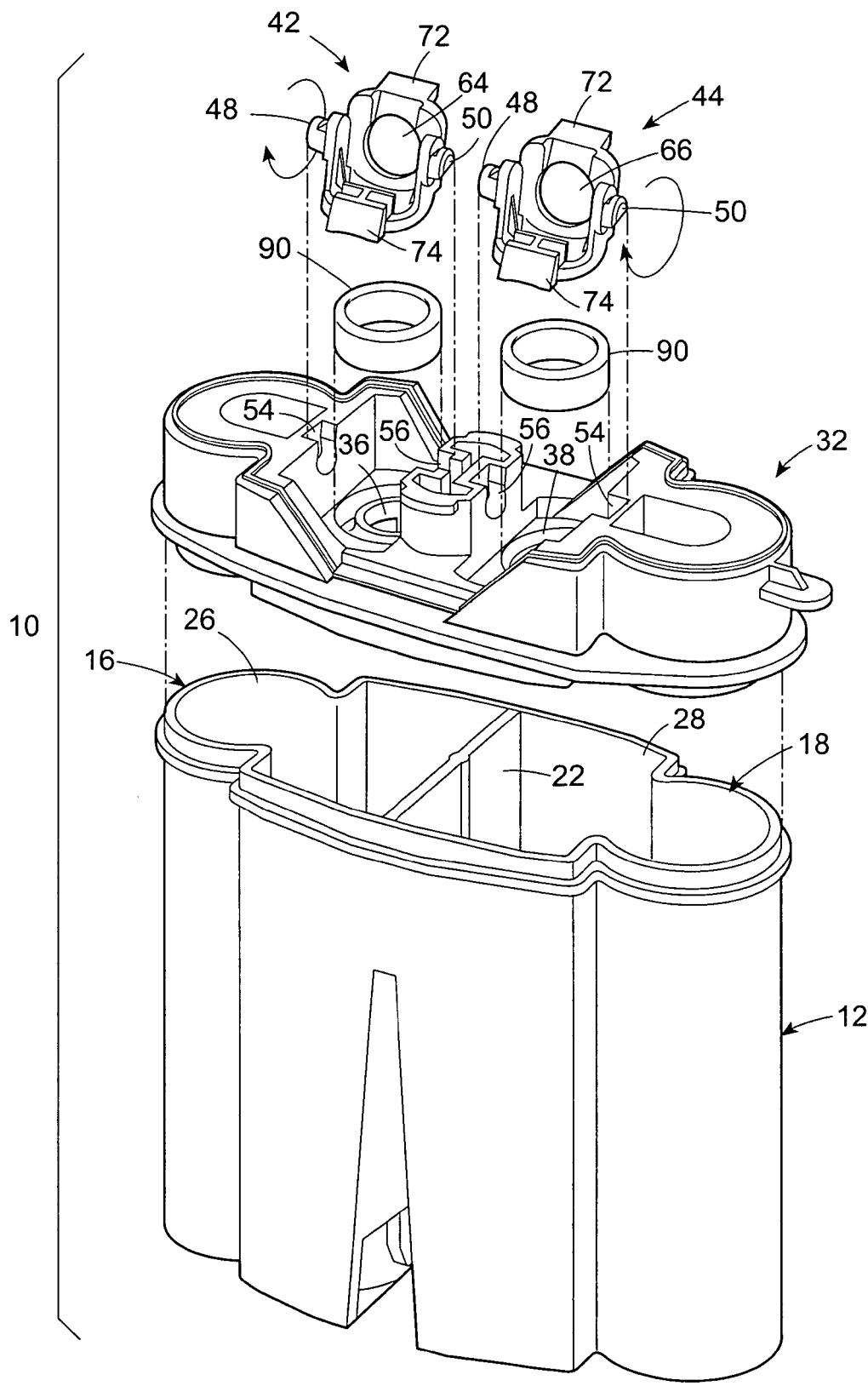
FIG. 1 is an exploded perspective view of a reagent package incorporating one embodiment of the invention.
Figure 3:
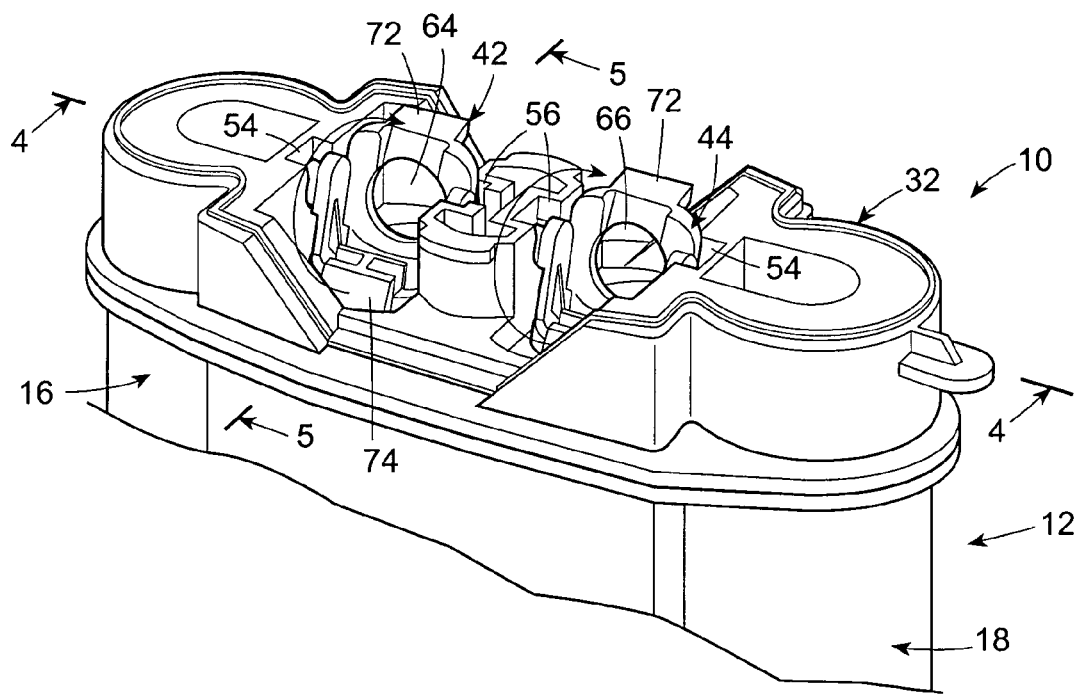
FIG. 3 is an elongated perspective detail of the components of FIG. 1 in assembled condition.

A reagent package incorporating one embodiment of the invention is generally indicated by the reference number 10 in FIGS. 1 and 3.

The reagent package 10 includes a container housing section 12 with two packaging sections 16 and 18 arranged side by side. An inner partition wall 22 (FIG. 1) divides the interior of container housing section 12 into two separate container chambers 26 and 28, one for each packaging section 16, 18. Although the packaging sections 16 and 18 are formed as an integral unit of the reagent package 10, the contents of the packaging section 16 and the chamber 26 cannot communicate with the contents of the packaging section 18 and the chamber 28.

Each packaging section 16 and 18 is similar in structure and function. If desired, any of the packaging sections 16 and 18 can be formed as a separate reagent package.

Figure 4:
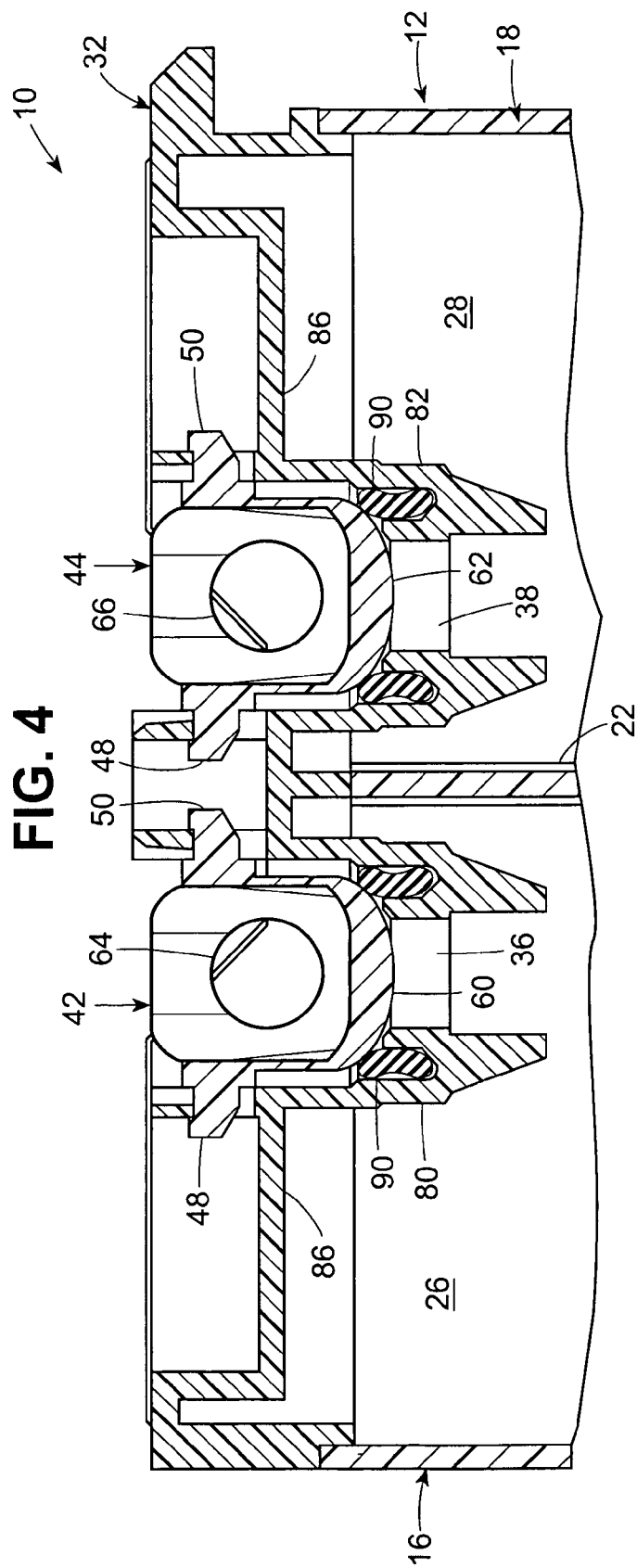
FIG. 4 is a sectional view taken on the line 4-4 of FIG. 3.

A container lid 32 (FIGS. 1 and 4) includes two chamber openings 36 and 38 to the respective chambers 26 and 28 when the container lid 32 is assembled to the container housing section 12 as shown in FIGS. 3 and 4. The container lid 32 also supports two identical rocker valves 42 and 44 (FIGS. 3 and 4) that are pivotable relative to the respective chamber openings 36 and 38.

Each rocker valve 42, 44 includes a pair of valve pivots 48 and 50 (FIGS. 1 and 4) supported in respective pivot cradles 54 and 56 (FIGS. 1 and 3) on the container lid 32. Each rocker valve 42 and 44 also includes a respective valve face 60 and 62 (FIG. 4) and respective valve openings 64 and 66.

Figure 5:
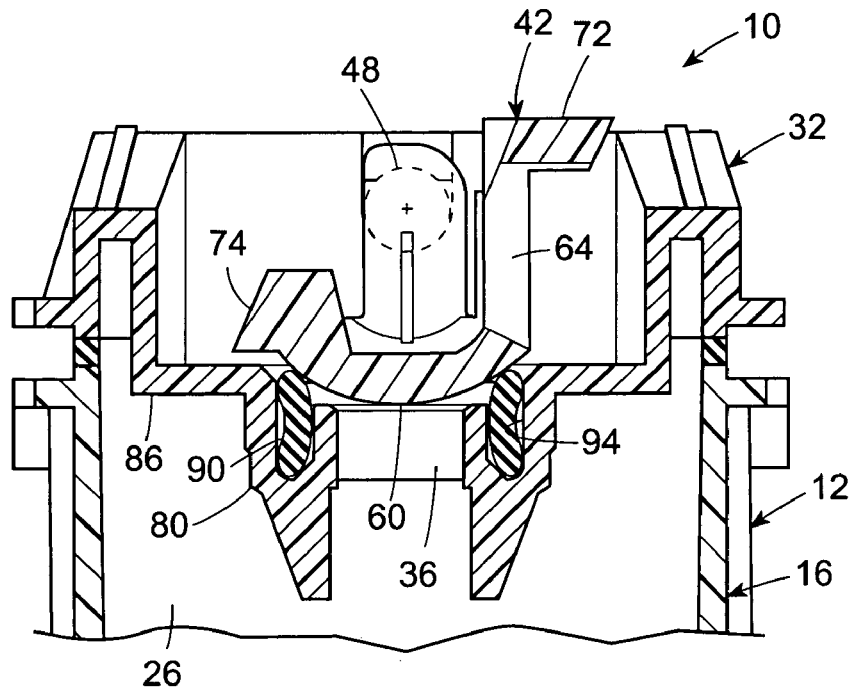
FIG. 5 is a sectional view taken on the line 5-5 of FIG. 3.
Figure 6:
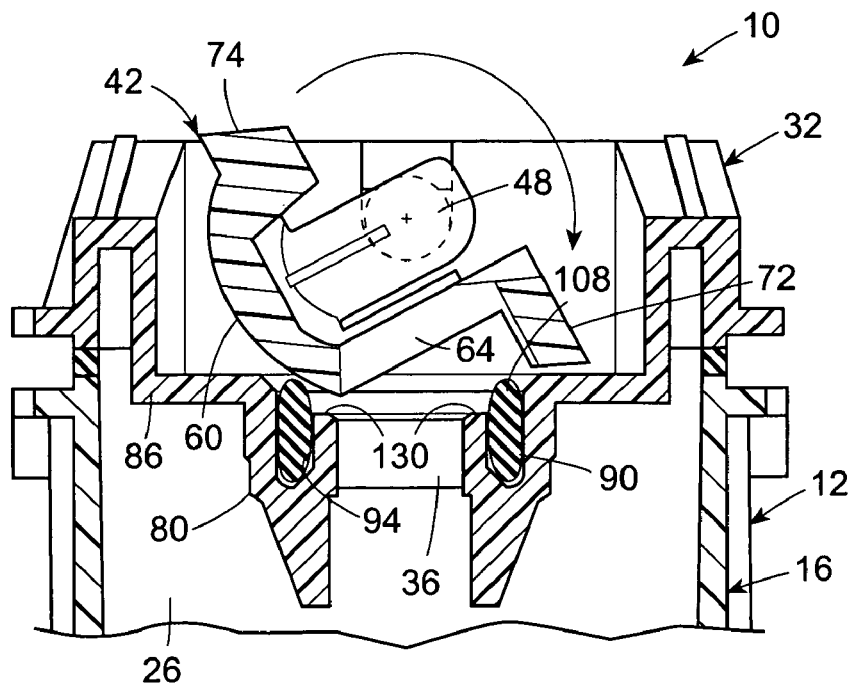
FIG. 6 is a view similar to FIG. 5 with the rocker valve in a valve open position; and, FIG. 7 is a simplified sectional detail of the reagent package lid without the rocker valve and annular cylindrical gasket.

The rocker valves 42 and 44 are pivotable between a valve open position, such as shown for example in FIG. 6, wherein the valve opening 64 aligns with the chamber opening 36 in the container lid 32, and a valve closed position (FIGS. 4 and 5) wherein the respective valve faces 60 and 62 cover the respective chamber openings 36 and 38.

Each of the rocker valves 42 and 44 include an actuation surface 72 (FIGS. 1, 3, 5 and 6) that receives a force for moving the valves 42, 44 to a valve open position and an actuation surface 74 that receives a force for moving the valves 42, 44 to a valve closed position. The actuation surfaces 72 and 74 receive an actuation force at predetermined time intervals by an actuator member (not shown) that exerts a downwardly directed force on the respective actuation surfaces 72, 74 to pivot the rocker valves 42 and 44 from a valve open condition to a valve closed condition and vice versa.

The chamber openings 36 and 38 extend through identical collars 80 and 82 (FIG. 4) that depend from a lid section 86.

Each of the chamber openings in the lid 32 is surrounded by an annular cylindrical gasket 90 seated in an annular channel 94 (FIGS. 5-7) formed in the respective collars 80 and 82. The annular cylindrical gasket is preferably formed of a suitable compressible material such as Nitrile-Buna-N 60 Durometer (Shore A).

Figure 2:
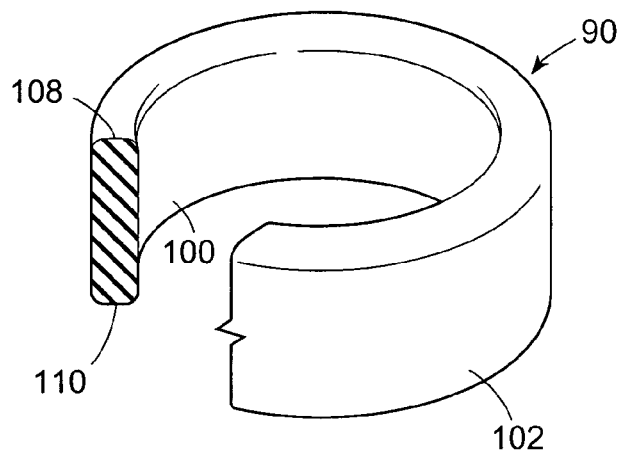
FIG. 2 is a perspective view of an annular cylindrical gasket thereof, with a broken away portion.

Referring to FIG. 2, the annular cylindrical gasket 90, in cross section, has inner and outer surfaces 100 and 102, and opposite curved end portions 108 and 110 of the same curvature.

Figure 7:
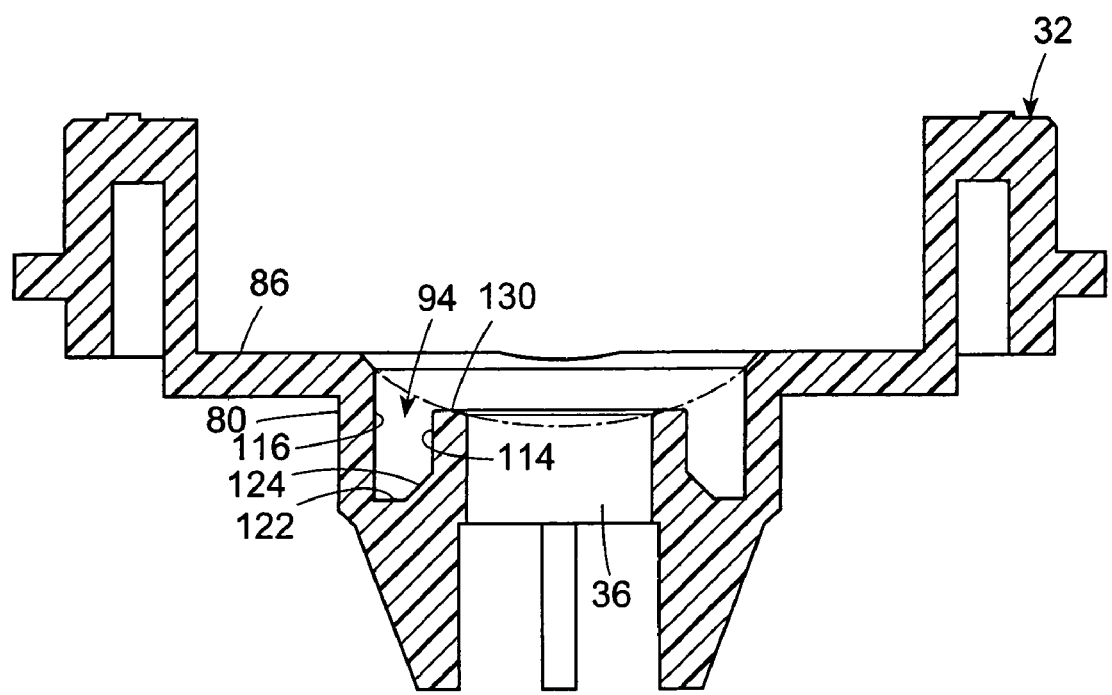

Referring to FIG. 7, the annular channel 94 includes a radially inner peripheral channel sidewall 114 and a radially outer peripheral channel sidewall 116. The annular channel 94 also includes a bottom portion 122 and an inclined peripheral wall 124 that intersects one of the channel sidewalls, preferably the inner channel sidewall 114 at an obtuse angle and also intersects the bottom portion 112. The inclined peripheral wall 124 can have an inclination of approximately 45° to the horizontal.

The inner peripheral sidewall 114 (FIG. 7) is of lesser height from the bottom portion 122 than the outer peripheral sidewall 116. The annular cylindrical gasket 90 (FIGS. 2, 5, 6 and 7) has an elevation from the end portion 108 to the end portion 110 that is greater than the height of the inner channel sidewall 114 from the bottom portion 122 to an inner end surface 130 (FIG. 7) of the collar 80.

Under this arrangement, there is a step down from an end portion 108 of the annular cylindrical gasket 90 to the inner end surface 130 of the collar 80 (FIG. 6). The step down between the end portion 108 of the annular cylindrical gasket 90 and the inner end surface 130 of the collar 80 enables the valve face 60 to engage the end surface 108 of the annular cylindrical gasket 90 without interfering with the collar 80, when the rocker valve 42 is in a valve closed position as shown in FIG. 5.

It has been found that a predetermined compressive engagement between the annular cylindrical gasket 90 and the valve face 60 that will permit a reagent valve actuation force of approximately 1.5 lbs. to move the rocker valve from a valve closed position to a valve open position and vice versa will also maintain a reagent evaporation rate of less than 0.05% per day in the reagent package 10.

Thus, when the rocker valve 42 is in a valve closed position as shown in FIG. 5, an actuator (not shown) can push down on the actuation surface 72 with a force of 1.5 lbs. or less to cause movement of the rocker valve 42 from the valve closed position of FIG. 5 to the valve open position of FIG. 6. A similar actuation force of 1.5 lbs. applied to the actuation surface 74 of the rocker valve 42 is sufficient to move the rocker valve from the valve open position of FIG. 6 to the valve closed position of FIG. 5.

An example of component dimensions of the reagent package 10 that provides the desired valve seal and the desired actuation force include a height of the gasket 94 from the end portion 108 to the end portion 110 of approximately 4.5 mm, an inner diameter of approximately 9 mm and an outer diameter of approximately 11.8 mm. The radius of curvature at the corners of the end portions 108 and 110 of the annular cylindrical gasket 90 can be approximately 0.7 mm.

The inner diameter of the channel 94 can be approximately 8.65 mm and the outer diameter approximately 12.45 mm. The distance from the channel bottom 122 to the end surface 130 can be approximately 3.21 mm and the vertical elevation of the inclined peripheral wall 124 can be approximately 0.88 mm.

The radius of curvature of the valve face 60 can be approximately 10.3 mm and the distance between the pivot axis of the valve pivots 48 and 50 and the end portion 108 of the annular cylindrical gasket 90 can be approximately 7.42 mm.

Under this arrangement, a predetermined compression is established between the rocker valve face 60 and the end portion 108 of the annular cylindrical gasket 90 that permits a 1.5 lb. actuation force to move the valve. Furthermore, the valve seal between the valve face 60 and the end portion 108 of the annular cylindrical gasket 90 provides a leak tight seal that ensures maintenance of the required evaporation rate.

In view of the above, it will be seen that the several objects of the invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. A reagent package comprising,
   a) a container having an inside chamber and an opening to said inside chamber,
   b) a rocker valve on said container at said opening, said rocker valve having a curved face portion and a pivot mounted on said container for pivotal movement of said curved face portion from a valve open position, wherein said rocker valve permits outside communication into the chamber through said container opening, to a valve closed position wherein said rocker valve closes said container opening to prevent outside communication into the chamber through the container opening,
   c) said container including an annular channel surrounding said container opening and a compressible annular cylindrical gasket seated in said channel, said compressible annular cylindrical gasket including a cross section which includes one end portion, another end portion opposite the one end portion, an inner radial surface and an outer radial surface, and an elevation from the one end portion to the other end portion which is greater than a radial gasket thickness measured between the inner radial surface and the outer radial surface of the cross section of the compressible annular cylindrical gasket, said compressible annular cylindrical gasket having said one annular end portion that engages said curved face portion when the curved face portion is moved from the valve open position to the valve closed position whereby, said one annular end portion is in annular sealing contact with the curved face portion of said rocker valve when the rocker valve is in the valve closed position,
   d) said annular channel including a radially inner peripheral channel sidewall and a radially outer peripheral channel sidewall, and a bottom portion, and
   e) said annular channel further including an inclined peripheral wall that intersects one of said channel sidewalls at an obtuse angle wherein movement of the curved face portion from the valve open position to the valve closed position deforms the compressible annular cylindrical gasket in a radial direction at each annular end portion within the annular channel.

2. The reagent package as claimed in claim 1 wherein the inclined peripheral wall does not intersect the other of said channel sidewalls.

3. The reagent package as claimed in claim 1 wherein the inclined peripheral wall also intersects the bottom portion of said channel.

4. The reagent package as claimed in claim 1 wherein the inclined peripheral wall intersects the radially inner peripheral channel sidewall.

5. The reagent package as claimed in claim 2 wherein the inclined peripheral wall intersects the radially inner peripheral channel sidewall.

6. The reagent package as claimed in claim 1 wherein the annular cylindrical gasket has spaced inner and outer cylindrical wall portions that each define a curved cylindrical surface.

7. The reagent package as claimed in claim 6 wherein said ring gasket has an opposite end portion that is of similar shape to the one end portion when said ring gasket is not subject to end-to-end compression.

8. The reagent package as claimed in claim 6 wherein the annular cylindrical gasket is in end-to-end compression and the opposite end portion of the annular cylindrical gasket is urged against the inclined peripheral wall and the bottom portion of said channel when the rocker valve is in the valve closed position, the end-to-end height of the annular cylindrical gasket being selected such that one end portion of the annular cylindrical gasket in sealing contact with the curved face portion of the rocker valve, exerts a predetermined force on the curved face of the rocker valve.

9. The reagent package as claimed in claim 1 wherein the annular cylindrical gasket is formed of rubber.

10. A reagent package comprising,
    a) a container having an inside chamber and an opening to said inside chamber,
    b) a rocker valve on said container at said opening, said rocker valve having a curved face portion and a pivot mounted on said container for pivotal movement of said curved face portion from a valve open position, wherein said rocker valve permits outside communication into the chamber through said container opening, to a valve closed position wherein said rocker valve closes said container opening to prevent outside communication into the chamber through the container opening,
    c) said container including an annular channel surrounding said container opening and a compressible annular cylindrical gasket seated in said channel, said compressible annular cylindrical gasket including a cross section which includes an upper end portion, a lower end portion opposite the upper end portion, an inner radial surface and an outer radial surface, and an elevation from the upper end portion to the lower end portion which is greater than a radial gasket thickness measured between the inner radial surface and the outer radial surface of the cross section of the compressible annular cylindrical gasket, the upper end portion engageable with the curved face portion of said rocker valve when the curved face portion of the rocker valve is moved from the valve open position to the valve closed position,
    d) said annular channel including a radially inner peripheral channel sidewall and a radially outer peripheral channel sidewall, and a bottom portion, and
    e) said annular channel further including an inclined peripheral wall that intersects the radially inner peripheral channel sidewall at an obtuse angle and also intersects the bottom portion of said channel wherein movement of the curved face portion from the valve open position to the valve closed position deforms the compressible annular cylindrical gasket in a radial direction within the annular channel.

11. The reagent package as claimed in claim 10 wherein the annular cylindrical gasket is in end-to-end compression and the opposite end portion of the annular cylindrical gasket is urged against the inclined peripheral wall and the bottom portion of said channel when the rocker valve is in the valve closed position, the end-to-end height of the annular cylindrical gasket being selected such that one end portion of the annular cylindrical gasket that is in sealing contact with the curved face portion of the rocker valve, exerts a predetermined force on the curved face of the rocker valve.

12. A method of sealing a valve controlled opening with a rocker valve comprising, (a) supporting a rocker valve for pivotal movement at an opening in a hollow member such that the rocker valve is pivotable with respect to said hollow member from a valve-open position, wherein the rocker valve permits communication into the hollow member through the opening, and a valve-closed position, wherein the rocker valve closes the opening in the hollow member to prevent outside communication into the hollow member through the opening, (b) providing the rocker valve with a curved face portion that blocks the opening in the hollow member when the rocker valve is in the valve-closed position, (c) forming an annular channel in the hollow member to encircle the opening in the hollow member and providing the annular channel with a radially inner peripheral channel sidewall, a radially outer peripheral channel sidewall, a bottom portion and an inclined peripheral wall that intersects one of the channel sidewalls at an obtuse angle, (d) providing a compressible annular cylindrical gasket in the annular channel, the compressible annular cylindrical gasket including a cross section which includes one end portion, an opposite end portion opposite the one end portion, an inner radial surface, an outer radial surface, an end-to-end height measured from the one end portion to the opposite end portion, and a radial gasket thickness measured between the inner radial surface and the outer radial surface of the cross section of the compressible annular cylindrical gasket, such that the one end portion of the compressible annular cylindrical gasket is at the bottom portion of the annular channel and the opposite end portion of the cylindrical gasket engages the curved face portion of the rocker valve when the rocker valve is in the valve-closed position, and (e) providing the annular cylindrical gasket with the end-to-end height being greater than the radial gasket thickness that enables the one end portion of the annular cylindrical gasket to be urged against the inclined peripheral wall portion and the bottom portion of the channel, the compressible annular cylindrical gasket to deform in a radial direction within the annular channel, and the opposite end portion to engage against the curved-face portion of the rocker valve when the rocker valve is moved from the valve open position to the valve closed position, to form a leak-tight seal with the rocker valve around the opening in the hollow member when the rocker valve is in the valve closed position.

13. The method of claim 12 wherein the step of forming the annular channel includes forming the inclined peripheral wall to also intersect the bottom portion of the annular channel.

14. The method of claim 13 wherein the step of forming the annular channel includes forming the inner peripheral wall to intersect the radially inner peripheral channel sidewall and the bottom portion of the channel.

15. The method of claim 12 including selecting the end-to-end height of the annular cylindrical gasket to enable the annular cylindrical gasket to exert a predetermined force on the curved face of the rocker valve when the rocker valve is in the valve-closed position.

16. The reagent package as claimed in claim 1 wherein the annular cylindrical gasket has an inner cylindrical surface and an outer cylindrical surface that are substantially parallel to each other when said rocker valve is in said valve open position.

17. The reagent package as claimed in claim 10 wherein the annular cylindrical gasket has an inner cylindrical surface and an outer cylindrical surface that are substantially parallel to each other when said rocker valve is in said valve open position.

18. The method of claim 12 including forming the annular cylindrical gasket with an inner cylindrical surface and an outer cylindrical surface that are substantially parallel to each other when the rocker valve is in the valve open position.

19. The reagent package of claim 1 wherein the annular channel includes a radial channel thickness which is greater than the radial gasket thickness and wherein the compressible annular cylindrical gasket deforms radially within the annular channel when said one annular end portion is in annular sealing contact with the curved face portion of said rocker valve in the valve closed position.

20. The reagent package of claim 10 wherein the annular channel includes a radial channel thickness measured between the radially inner peripheral channel sidewall and the radially outer peripheral channel sidewall, which is greater than the radial gasket thickness.

21. The method of claim 12 wherein the annular channel includes a radial channel thickness measured between the radially inner peripheral channel sidewall and the radially outer peripheral channel sidewall, and the radial channel thickness is greater than the radial gasket thickness.

* * * * *